United States Patent
Miyazaki et al.

(10) Patent No.: US 9,545,206 B2
(45) Date of Patent: Jan. 17, 2017

(54) NON-CONTRAST MRI WITH DIFFERENTIATION OF ISCHEMIC, INFARCT AND NORMAL TISSUE

(75) Inventors: Mitsue Miyazaki, Mount Prospect, IL (US); Xiangzhi Zhou, Vernon Hills, IL (US); Tsutomu Hoshino, Palm Harbor, FL (US)

(73) Assignee: TOSHIBA MEDICAL SYSTEMS CORPORATION, Otawara-shi, Tochigi-ken (JP)

(*) Notice: Subject to any disclaimer, the term of this patent is extended or adjusted under 35 U.S.C. 154(b) by 0 days.

(21) Appl. No.: 13/587,294

(22) Filed: Aug. 16, 2012

(65) Prior Publication Data

US 2014/0050379 A1 Feb. 20, 2014

(51) Int. Cl.
| | |
|---|---|
| A61B 5/026 | (2006.01) |
| A61B 5/055 | (2006.01) |
| G01R 33/563 | (2006.01) |
| A61B 5/00 | (2006.01) |

(52) U.S. Cl.
CPC ............ *A61B 5/0263* (2013.01); *A61B 5/055* (2013.01); *G01R 33/56366* (2013.01); *A61B 5/7289* (2013.01); *A61B 2576/023* (2013.01)

(58) Field of Classification Search
CPC .... G01R 33/56366; A61B 6/507; A61B 5/055
USPC ............ 600/400, 419; 382/130, 131
See application file for complete search history.

(56) References Cited

U.S. PATENT DOCUMENTS

| | | | | |
|---|---|---|---|---|
| 5,685,305 | A | * | 11/1997 | Moonen et al. ............ 600/419 |
| 6,295,465 | B1 | * | 9/2001 | Simonetti ............ 600/413 |
| 7,505,614 | B1 | * | 3/2009 | De La Torre-Bueno ............ G06F 19/324 382/128 |
| 2008/0038197 | A1 | * | 2/2008 | John et al. ............ 424/9.1 |
| 2011/0071382 | A1 | * | 3/2011 | Miyazaki et al. ............ 600/413 |

FOREIGN PATENT DOCUMENTS

| | | |
|---|---|---|
| JP | 2000-342555 | 12/2000 |
| JP | 2001-231764 | 8/2001 |
| JP | 2010-022813 | 2/2010 |
| JP | 2010-201154 | 9/2010 |

(Continued)

OTHER PUBLICATIONS

Warmuth, Carsten, et al. "Dynamic spin labeling angiography in extracranial carotid artery stenosis." American journal of neuroradiology 26.5 (2005): 1035-1043.*

(Continued)

*Primary Examiner* — Chan Park
*Assistant Examiner* — Geoffrey E Summers
(74) *Attorney, Agent, or Firm* — Nixon & Vanderhye P.C.

(57) ABSTRACT

Elicited MRI signals are processed into MR image data in conjunction (a) with use of an initial spatially-selective RF tag pulse (tag-on) and (b) without use of an initial spatially-selective NMR RF tag pulse (tag-off) in respectively corresponding data acquisition subsequences. Multi-dimensional tag-on and tag-off data acquisition subsequences are used for each of plural time-to-inversion (TI) intervals without using an injected contrast agent. Acquired image data sets are subtracted for each TI interval to produce difference values as a function of time representing blood perfusion for the ROI that differentiates between normal, ischemic and infarct tissues.

15 Claims, 10 Drawing Sheets

(56) References Cited

FOREIGN PATENT DOCUMENTS

JP 2011-067696 4/2011
JP 2011-083592 4/2011

OTHER PUBLICATIONS

Bokkers, R. P. H., et al. "Arterial spin-labeling MR imaging measurements of timing parameters in patients with a carotid artery occlusion." American Journal of Neuroradiology 29.9 (2008): 1698-1703.*

MacIntosh, B. J., et al. "Multiple inflow pulsed arterial spin-labeling reveals delays in the arterial arrival time in minor stroke and transient ischemic attack." American Journal of Neuroradiology 31.10 (2010): 1892-1894.*

Miyazaki, Mitsue, and Vivian S. Lee. "Nonenhanced MR Angiography 1." Radiology 248.1 (2008): 20-43.*

Kim, et al., "Relationship of MRI Delayed Contrast Enhancement to Irreversible Injury, Infarct Age, and Contractile Function," Circulation Journal of the American Heart Association, pp. 1991-2002 (Nov. 9, 1999).

Nandalur, et al., "Diagnostic Performance of Stress Cardiac Magnetic Resonance Imaging in the Detection of Coronary Artery Disease," Journal of the American College of Cardiology: Cardiac Imaging, vol. 50, No. 14, pp. 1343-1353 (Oct. 2, 2007).

Dall'Armellina, et al., "CMR for characterization of the myocardium in acute coronary syndromes," Nature Reviews, Cardiology, vol. 7, pp. 624-636 (Nov. 2010).

Cerqueira, et al., "Standardized Myocardial Segmentation and Nomenclature for Tomographic Imaging of the Heart: A Statement for Healthcare Professionals From the Cardiac Imaging Committee of the Council on Clinical Cardiology of the American Heart Association," vol. 105, pp. 539-542 (2002).

Ortiz-Perez, et al., "Correspondence Between the 17-Segment Model and Coronary Arterial Anatomy Using Contrast-Enhanced Cardiac Magnetic Resonance Imaging," Journal of the American College of Cardiology: Cardiovascular Imaging, vol. 1, No. 3, pp. 282-293 (May 2008).

International Search Report issued Sep. 17, 2013 in PCT/JP2013/071733.

* cited by examiner

NON-CONTRAST MRI WITH DIFFERENTIATION OF ISCHEMIC, INFARCT AND NORMAL TISSUE

FIELD

The subject matter below relates generally to magnetic resonance imaging (MRI) apparatus and process. In particular, the MRI apparatus and method described below provide non-contrast MRI with differentiation between ischemic, infarct and normal tissues (e.g., myocardium).

DETAILED DESCRIPTION OF EXEMPLARY EMBODIMENTS

Figure 1:
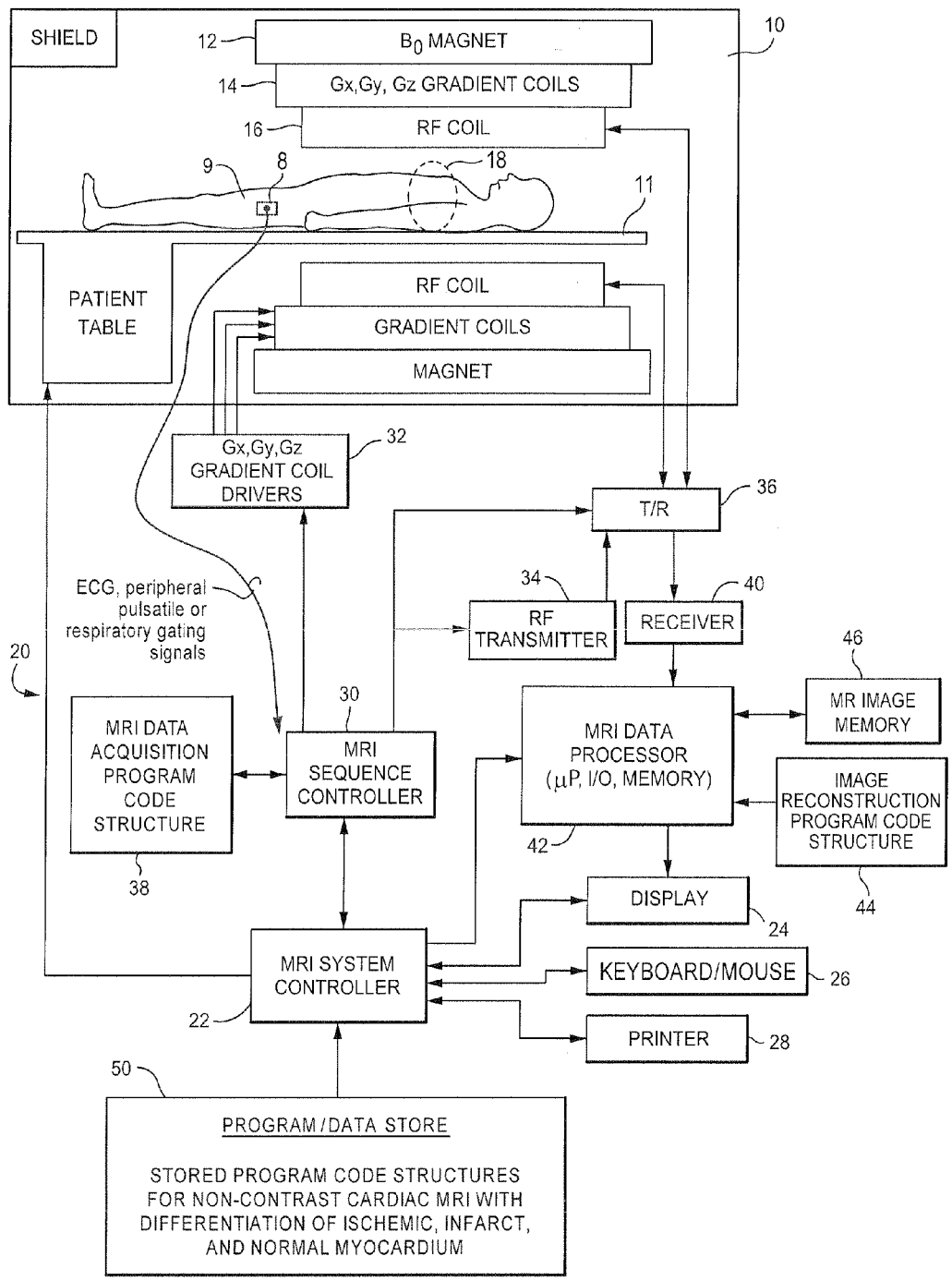
FIG. 1 is a high-level schematic block diagram of an exemplary MRI system configured to provide non-contrast cardiac MRI with differentiation between ischemic, infarct and normal myocardium tissues.

The MRI system shown in FIG. 1 includes a gantry 10 (shown in schematic cross-section) and various related system components 20 interfaced therewith. At least the gantry 10 is typically located in a shielded room. The MRI system geometry depicted in FIG. 1 includes a substantially coaxial cylindrical arrangement of the static field Bo magnet 12, a Gx, Gy and Gz gradient coil set 14 and an RF coil assembly 16. Along the horizontal axis of this cylindrical array of elements is an imaging region 18 shown as substantially encompassing the anatomy of interest (i.e., region of interest or "ROI") for a patient 9 (e.g., the heart for cardiac MRI) supported by a patient bed or table 11.

An MRI system controller 22 has input/output ports connected to display 24, keyboard/mouse 26 and printer 28. As will be appreciated, the display 24 may be of the touch-screen variety so that it provides control inputs as well.

The MRI system controller 22 interfaces with MRI sequence controller 30 which, in turn, controls the Gx, Gy and Gz gradient coil drivers 32, as well as RF transmitter 34 and transmit/receive switch 36 (if the same RF coil is used for both transmission and reception). As those skilled in the art will appreciate, many different types of RF coils (e.g., whole body coils, surface coils, birdcage boils, coil arrays, etc.) may be employed to transmit and/or receive RF signals to/from the ROI in the imaging volume. As will also be appreciated, one or more suitable physiological transducers 8 may be affixed to the patient's body to provide ECG (electrocardiogram), respiratory and/or peripheral pulsatile gating signals to the MRI sequence controller 30. The MRI sequence controller 30 also has access to suitable program code structure 38 for implementing MRI data acquisition sequences already available in the repertoire of the MRI sequence controller 30—e.g., to generate non-contrast cardiac MRI tissue images using operator and/or system inputs defining particular MRI data acquisition sequence parameters, one or more ROI, etc.

The MRI system 20 includes an RF receiver 40 providing input to data processor 42 so as to create processed image data which may be sent to display 24. The MRI data processor 42 is also configured for access to image reconstruction program code structure 44 and to MR (magnetic resonance) image memory 46 (e.g., for storing MR image data derived from processing in accordance with the exemplary embodiments and the image reconstruction program code structure 44).

Also illustrated in FIG. 1 is a generalized depiction of an MRI system program/data store 50 where stored program code structures (e.g., for non-contrast cardiac MRI capable of differentiating between ischemic, infarct and normal myocardium tissues), as well as a related graphical user interface (GUI), operator inputs to same, etc., which are stored in computer readable storage media accessible to the various data processing components of the MRI system. As those in the art will appreciate, the program store 50 may be segmented and directly connected, at least in part, to different ones of the system 20 processing computers having most immediate need for such stored program code structures in their normal operation (i.e., rather than being commonly stored and connected directly to the MRI system controller 22).

Indeed, as those skilled in the art will appreciate, the FIG. 1 depiction is a very high-level simplified diagram of a typical MRI system with some modifications so as to practice exemplary embodiments to be described hereinbelow. The system components can be divided into different logical collections of "boxes" and typically comprise numerous digital signal processors (DSP), microprocessors, special purpose processing circuits (e.g., for fast A/D conversions, fast Fourier transforming, array processing, etc.). Each of those processors is typically a clocked "state machine" wherein the physical data processing circuits progress from one physical state to another upon the occurrence of each clock cycle (or predetermined number of clock cycles).

Not only does the physical state of processing circuits (e.g., CPUs, registers, buffers, arithmetic units, etc.) progressively change from one clock cycle to another during the course of operation, the physical state of associated data storage media (e.g., bit storage sites in magnetic storage media) is transformed from one state to another during operation of such a system. For example, at the conclusion of an MR imaging reconstruction process, an array of computer-readable accessible data value storage sites (e.g., multi-digit binary representations of pixel values) in physical storage media will be transformed from some prior state (e.g., all uniform "zero" values or all "one" values) to a new state wherein the physical states at the physical sites of such an array (e.g., of pixel values) vary between minimum and maximum values to represent real world physical events and conditions (e.g., the tissues of a patient over an imaged region space). As those in the art will appreciate, such arrays of stored data values represent and also constitute a physical structure—as does a particular structure of computer control program codes that, when sequentially loaded into instruction registers and executed by one or more CPUs of the MRI system 20, cause a particular sequence of operational states to occur and be transitioned through within the MRI system.

The exemplary embodiments described below provide improved ways to acquire and/or process MRI data acquisitions and/or to generate and display MR images.

Use of an injected gadolinium (Gd)-based contrast agent (possibly in association with an injected stress perfusion agent) is known, but use of such contrast agents is often not an acceptable MRI technique for detecting infarct and ischemic lesions in myocardium. Late gadolinium contrast enhancement (LGE) is based on measuring a difference between normal and infarct myocardium by observing MRI T1-contrast (wash-out) of the gadolinium contrast agent via observed MRI signals from the myocardium after injection. In order to get a realistic observation of myocardium under stress, such stress may be induced by patient physical exercise or injected drug-induced stress (intended to cause increase in heart rate, dilation of cardiovascular blood vessels, etc., similar to that caused by physical exercise) so as to hopefully better observe blood flow abnormalities under such transient stress situations.

We have now discovered a way to avoid use of such contrast agents by achieving a non-contrast (i.e., without injection of a chemical contrast agent) MRI technique for producing myocardium perfusion curves/table data that can be used to distinguish between normal myocardium, ischemic myocardium and infarct myocardium. Indeed, even revascularized infarct myocardium (treated with revascularized techniques such as stent insertions into blood vessels, surgical bypass blood vessel operations, etc.) may be distinguished. In accordance with exemplary embodiments, such myocardium distinctions can be made within any desired region of interest (e.g., an operator-defined arbitrary region of interest, a standard American Heart Association (AHA) segment, a single pixel, etc.).

Although injection of a contrast agent (e.g., gadolinium-based) is avoided, it may still be desirable to use exemplary embodiments in combination with patient stress (either exercise-induced or drug-induced) so as to better detect abnormalities that may exist or be more prominent only during such stressed situations.

In exemplary embodiments, a set of "tag-on" (2D or 3D) MRI k-space data is acquired after an incoming volume of blood has been "tagged" with an initial spatially selective RF pulse (e.g. typically a spatially selective 180° inversion pulse) where the data acquisition subsequence starts after a given time to inversion (TI) delay time. A similar set of "tag-off" MRI data is also acquired using the same TI delay interval—but without the initial spatially selective RF tagging pulse. This technique is sometimes known in the art as black blood time to inversion (BBTI) imaging. A sequence of such tag-on/tag-off data sets for each of plural TI times is acquired in k-space.

For each given TI time, 2D/3D Fourier Transform reconstructed spatial domain tag-on and tag-off image data sets (i.e., the result of well known 2DFT/3DFT reconstruction processes) are subtracted (e.g., on a pixel-by-pixel basis) to provide BBTI blood perfusion images where blood perfusion (MR signal strength) as a function of time can be plotted or tabulated. For any given region of interest (e.g., an AHA segment, arbitrary operator-defined ROI or even a single pixel), a plot of the time sequence of data values provides a blood perfusion curve as a function of time which provides several dimensions of differentiation between perfusion curves for "normal" myocardium, abnormal, ischemic myocardium, infarct myocardium—and even revascularized (treated) ischemic myocardium. As will be expected, infarct myocardium shows no perfusion (i.e., no peak or increase in detected MRI signal strength). However, ischemic myocardium has a time-delayed peak flow time of occurrence, as well as less detected signal intensity, when compared to normal (or revascularized) myocardium. Accordingly, ischemic areas can be distinguished based upon time and/or amplitude (or even integrated area under the curve) comparisons and/or comparisons to predetermined thresholds, etc.

A perfusion curve and/or a corresponding data table pertaining to a region of interest (e.g., a predetermined AHA myocardium segment or an arbitrary operator-indicated ROI or even a single pixel) that includes distinguishing characteristics so that the MRI results (e.g., as displayed to an operator or stored data for later display to others) can differently depict the ROI as representing normal, ischemic, infarct or even revascularized myocardium—all without use of any injected contrast agent (e.g., gadolinium).

Figure 2:
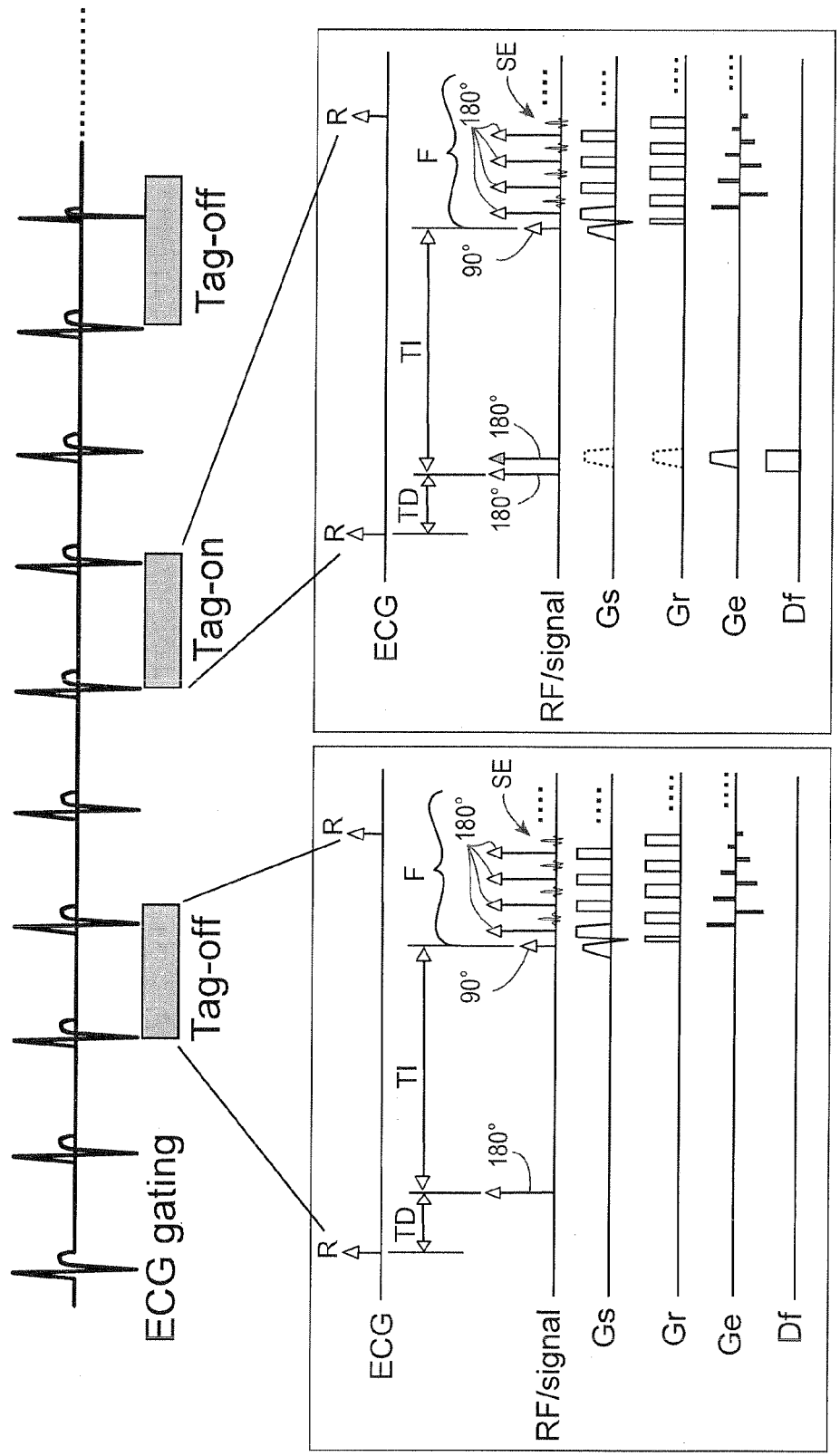
FIG. 2 is a schematic depiction of a first exemplary tag-on, tag-off MRI data acquisition sequence for use in the system of FIG. 1.
Figure 8:
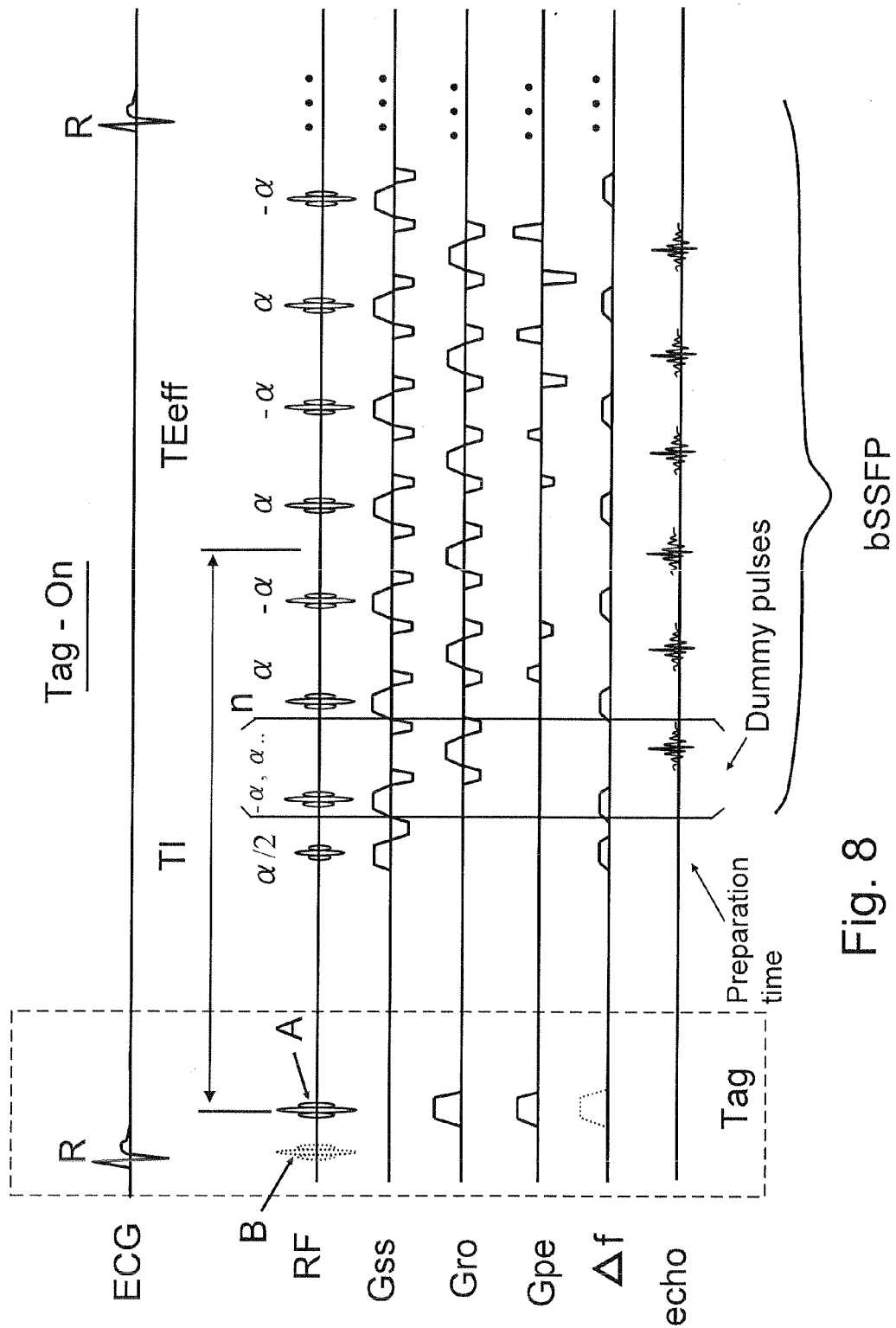
FIGS. 8-10 are schematic depictions of balanced steady state free precession (bSSFP) tag-on, tag-off and Tag-on/Tag-off alternating MRI data acquisition sequences for use in the system of FIG. 1.
Figure 9:
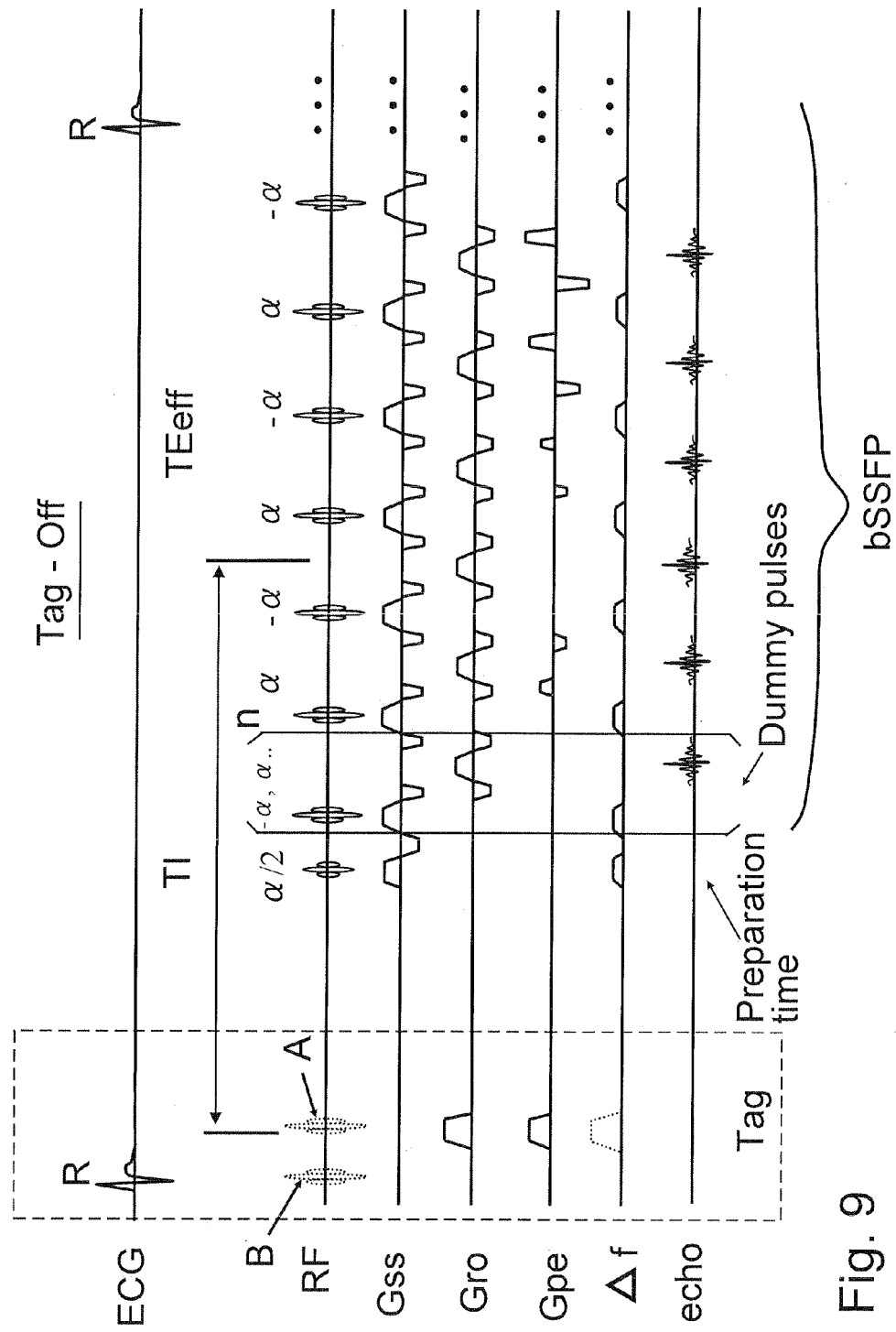
Figure 10:
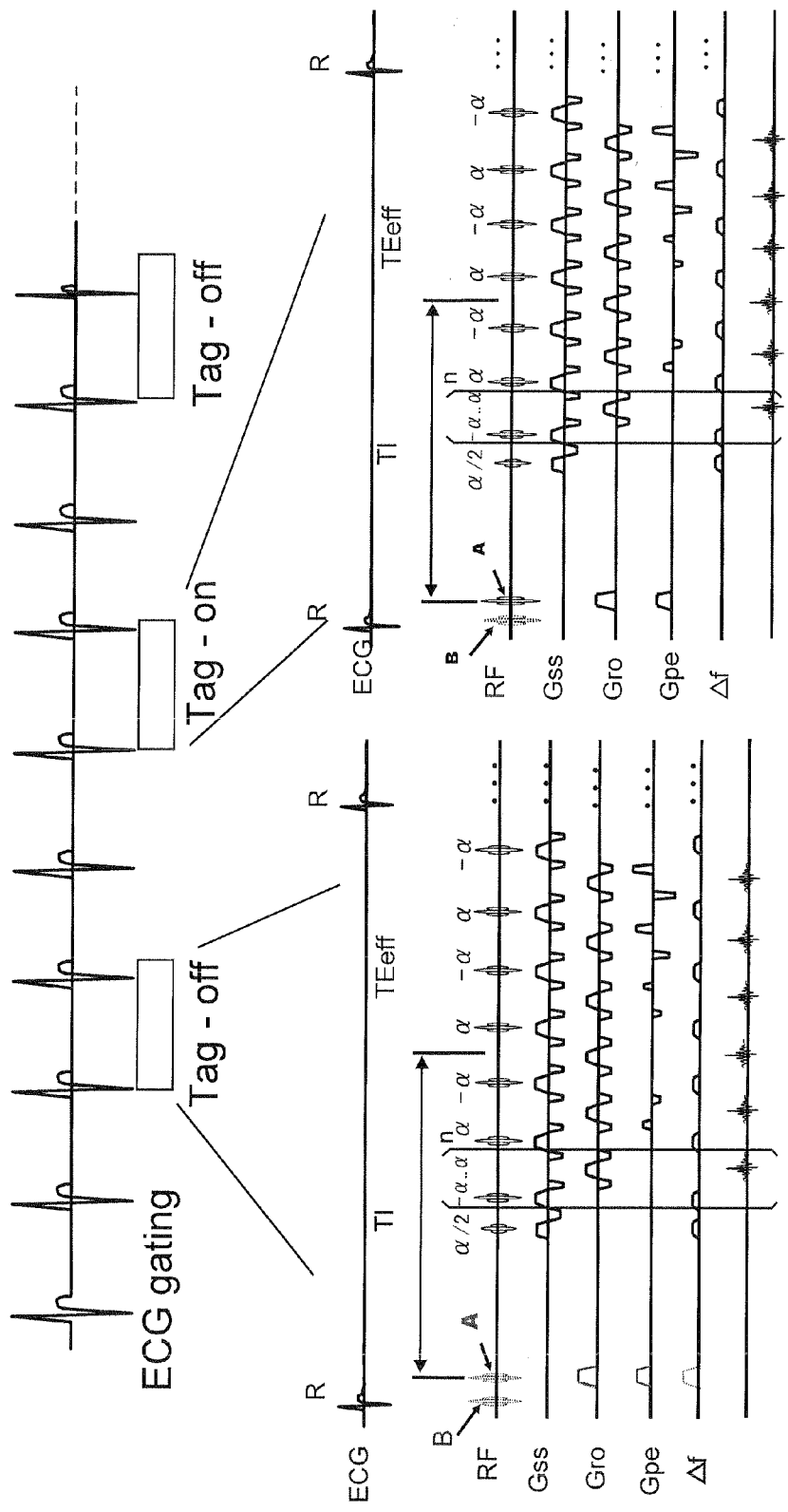

In an exemplary data acquisition sequence depicted at FIG. 2, electrocardiogram (ECG) gating is used so as to synchronize both "tag-off" and "tag-on" subsequences as depicted. In the tag-off subsequence shown to the left-lower side of FIG. 2, a short initial fixed time delay TD is employed to ensure that that the data acquisition subsequence begins its active phase during a desired diastole portion of the RST ECG signal. After delay TD, a non-selective 180° nuclear magnetic resonance (NMR) RF nutation pulse is employed (to help suppress background signals from a subsequent difference image because the signal from myocardium is relatively small, e.g., about 10% of the total MRI signal). The active phase of the actual data acquisition subsequence may, if desired, begin with a preparation pulse (e.g., a fat suppression pulse), followed by a desired data acquisition subsequence F initiated with a slice-selective (e.g., $\alpha°$ -typically 45° or) 90° NMR nutation pulse to initiate a desired MRI data acquisition subsequence F, e.g., a sequence of slice-selective 180° RF nutation refocusing pulses to elicit intervening RF spin echo (SE) responses during readout gradient Gr pulses, each spin echo being preceded by a phase encoding Ge magnetic gradient pulse (which is varied for different echoes so as to elicit data for a respectively corresponding line in k-space). As those in the art will appreciate, such known MRI data acquisition subsequences might be, e.g., of the balanced steady-state free precession (bSSFP) type (presently preferred as shown in FIGS. 8-10) or of the fast spin echo (FSE) type or possibly of other types.

The tag-on data acquisition subsequence depicted at the right-lower side of FIG. 2 is similar to the tag-off subsequence—except that, after delay TD, there is also a spatially selective "tagging" 180° RF nutation pulse (e.g., perhaps at an oblique angle as represented by the dotted concurrent gradient pulses and the Df frequency offset pulse as depicted). As those in the art will appreciate, this will, in effect, revert a predetermined inflowing volume of blood back to a non-inverted magnetization orientation—thus "tagging" this inflowing volume of blood so that it will generate different MR signal responses than for the tag-off subsequence as the RF tagged flowing blood MR nuclei enter into the downstream region of interest (ROI).

Figure 3:
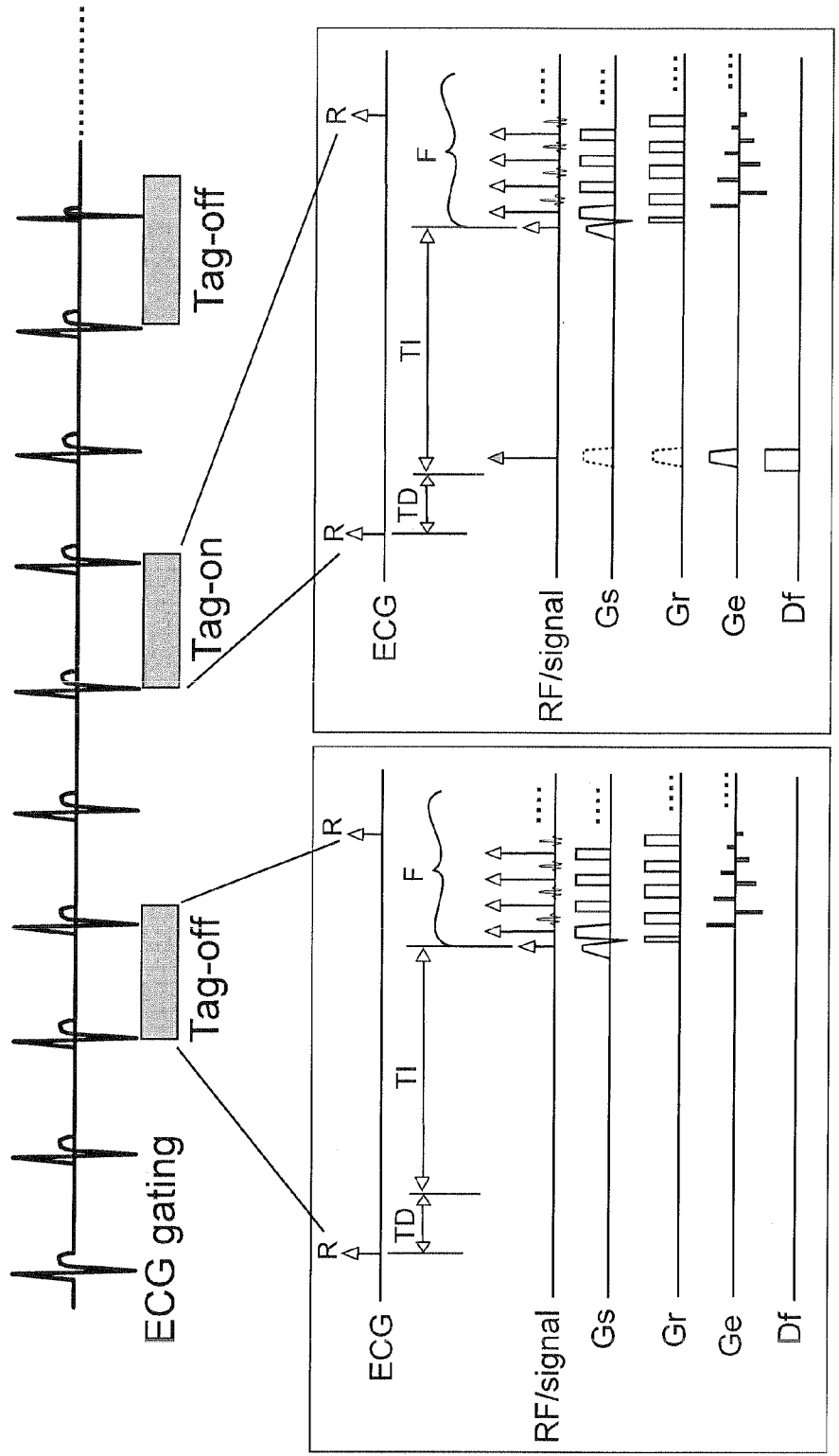
FIG. 3 is a schematic depiction of a second exemplary tag-on, tag-off MRI data acquisition sequence for use in the system of FIG. 1.

The tag-on/tag-off alternate acquisition subsequences depicted in FIG. 3 are the same as those depicted in FIG. 2, except that, as will be observed, there is no initial nonselective 180° nutation pulse (in either tag-on or tag-off subsequences) for background suppression purposes.

As depicted in dotted lines in both FIGS. 2 and 3, to achieve a desired oblique orientation for the spatially selective 180° tag-on nutation pulse, there may be concurrent usage of differently chosen magnitude Gs, Gr and Ge magnetic gradient pulses.

Figure 4:
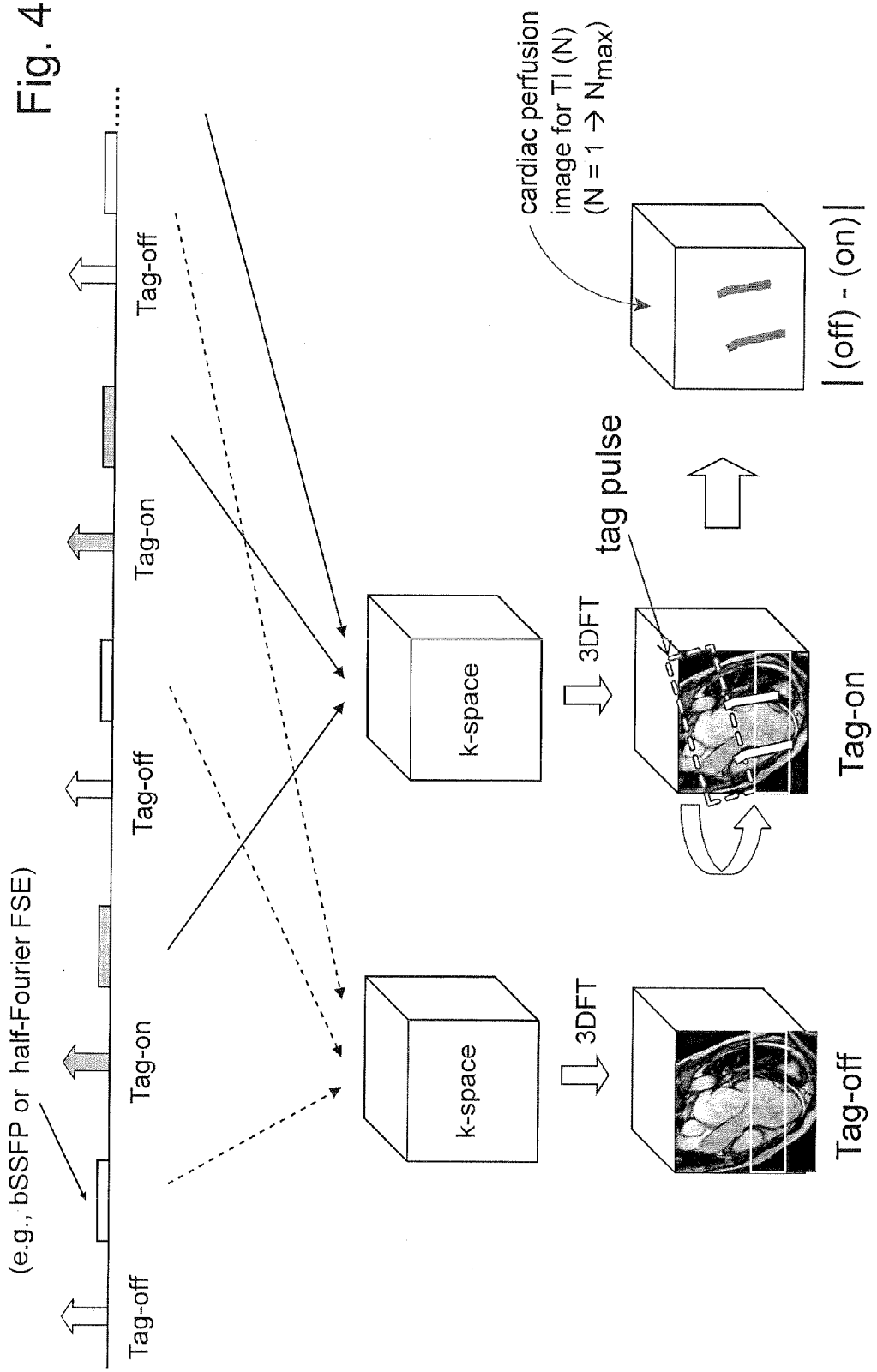
FIG. 4 is a schematic illustration of tag-on/tag-off 2D/3D data acquisition for k-space, 2D/3D Fourier transformation to the spatial domain and subtraction of the reconstructed tag-off and tag-on image data so as to produce blood perfusion image data in at least one region of interest (ROI) in accordance with the exemplary embodiments of FIGS. 1-3.

In the exemplary three-dimensional data acquisition sequence of alternate tag-on/tag-off subsequences depicted at FIG. 4, as those in the art will appreciate, one eventually gathers sufficient k-space data for both tag-off and tag-on conditions to permit tag-on and tag-off image constructions into the spatial domain (e.g., using a three-dimensional Fourier Transform technique well known in the art if a 3D data acquisition sequence has been utilized). The difference between the reconstructed tag-off and tag-on images for a desired region of interest then results from differencing the spatial domain tag-on/tag-off images (in either order of subtraction with the absolute value of the difference being utilized). This results in a difference image representing cardiac perfusion for some particular TI value. As depicted in FIG. 4, each cardiac perfusion image is for a particular TI(N) value. However, the same process will be repeated for multiple different TI values (i.e., as N varies from one to a maximum number). As will be appreciated, the TI values utilized and the intervals between them can be among the operator-controlled parameters at the outset of the entire image process.

Figure 5:
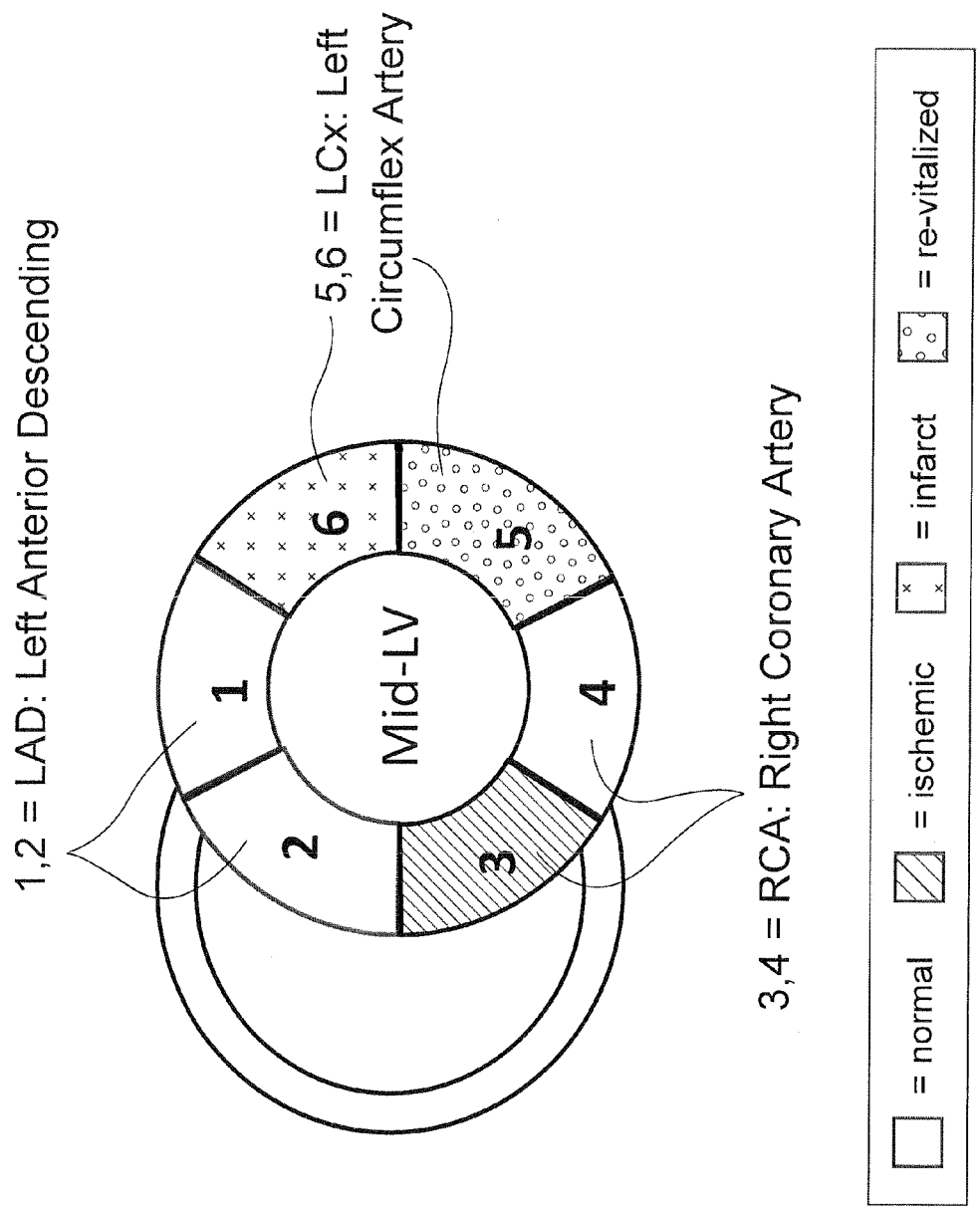
FIG. 5 is a schematic depiction of myocardial tissue segmentation for a short axis cross-section of left ventricular myocardial perfusion function (in accordance with an American Heart Association (AHA) segmentation standard), any such AHA segment being a possible ROI in the exemplary embodiments of FIGS. 1-4.

FIG. 5 depicts a short-axis left ventricle segmented AHA model where numbered segments 1-6 have been predefined to represent particular parts of the myocardium. This type of segmented display is commonly referred to as a "Bull's Eye" display—and plural such can be superimposed in concentric fashion (e.g., to concurrently depict base, mid and upper short-axis cross-sections of myocardium). If these segments have been chosen as regions of interest (e.g., as may be done by system default), then the exemplary embodiments permit these different regions of interest to be depicted differently on an operator/doctor screen and/or as represented by tabular table data entries or the like. For example, as shown in FIG. 5, segment 3 has been determined and displayed as ischemic myocardium, while segment 6 has been determined and displayed as infarct myocardium, while segment 5 has been determined and displayed as revitalized myocardium—while all other displayed segments are "normal".

Figure 6:
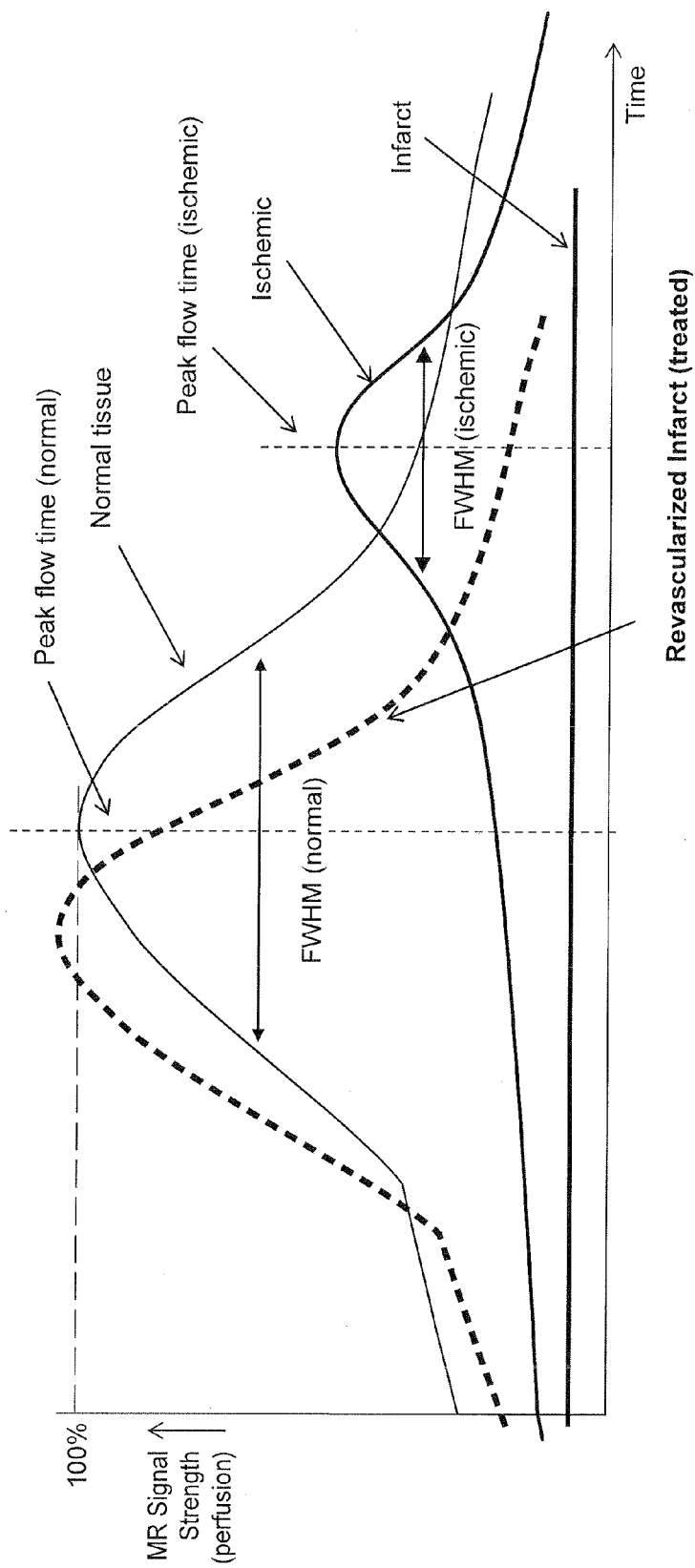
FIG. 6 depicts an exemplary plot of acquired magnetic resonance (MR) signal strength (representing blood perfusion) as a function of time illustrating how exemplary non-contrast cardiac MRI perfusion data for a given region of interest (perhaps down to a single pixel ROI) can be analyzed to distinguish between normal myocardium, ischemic myocardium and infarct myocardium—as well as revascularized infarct (treated) myocardium.

In the exemplary embodiments, such differentiation between these types of myocardial tissue, without use of contrast agents, becomes possible because the acquired perfusion data using variable TI intervals in a BBTI technique provides sufficient data to, in effect, plot the received MR perfusion signal strength for any desired ROI as a function of time, as depicted schematically at FIG. 6. Here, it will be seen that normal myocardium has a certain detectable peak flow time as represented by the mid-point of its full-width half-magnitude (FWHM) dimension—while ischemic myocardium has a temporally displaced later peak flow time, a smaller amplitude and smaller FWHM. Of course, the infarct myocardium, as would be expected, exhibits no peak at all (if, in fact, there is any detectable perfusion response at all). At the same time, as depicted in FIG. 6, revascularized previously infarct myocardium (i.e., after treatment such as by installation of stents and/or surgical bypass procedures) can be expected to have a yet earlier peak flow time in the temporal domain and possibly a slightly higher peak flow magnitude. As will be appreciated from FIG. 6, the integrated area under the curve (e.g., flow quantity) may also be used to distinguish between different kinds of myocardium.

While the presently preferred method of distinguishing between different type of myocardium relies primarily upon peak flow temporal distinctions, it will be appreciated that magnitude and/or integrated area under the curve and/or various combinations and permutations of these three possible distinguishing characteristics may be used to distinguish between these different types of myocardial tissue—all without using an injected chemical contrast agent.

Normal mean transit time, calculated from the FWHM (full-width at half-maximum), and the peak flow time can be tabulated for any specified ROI. As those in the art will appreciate, the acquired data points can be best-fitted to a curve and/or directly analyzed (e.g., to provide FWHM/peak time measurements) using conventional curve fitting and analysis techniques. Arbitrary signal intensity units can be indicated as a percent of the normal signal, which is assumed to be, e.g., 100%. As a result of such myocardium analysis, a table of peak flow time (e.g., FWHM) and area under the perfusion curve can be provided for each AHA myocardium segment, as well as any other desired and specified ROI #1, ROI #2, and so on (even down to a single pixel, if desired).

For example, if the perfusion difference image data is computed on a pixel-by-pixel basis, then the difference values for all pixels in a particular ROI can be added together or averaged or otherwise combined (or analyzed) to provide a single overall perfusion curve for that ROI. Of course, one could display all pixels of the ROI as individually shaded or colored to represent different tissue types.

The exemplary embodiments are based on non-contrast perfusion MRI where it is possible to resolve, e.g., in a few tens of milliseconds scale increments of tagged blood flow over a few hundred milliseconds (e.g., perhaps up to 1,000 ms of suitable heartbeat cycle is available), which was not possible to observe in fast pass Gd contrast perfusion MRI where the best time resolution is on the order of only a couple of seconds (e.g., 2,000 ms).

The exemplary embodiments permit depicting blood flows of a desired temporal resolution by controlling the TI time delay for different sets of data acquisition subsequences. One can use TI times of, e.g., minimum initial TI values such as 100 ms, followed by TI times of 200 ms, 300 ms, 400 ms, 500 ms, 600 ms, 800 ms, 1,000 ms and 1,200 ms. One can also use any desired different sequence of TI values, e.g., 100, 200, 250, 300, 350, 375, 400, 425, 450, 475, 500, 600, 800 and 1,000 ms. The range of coverage for each tag-on or tag-off subsequence is one RR interval of the ECG signal (e.g., perhaps 1,000 ms for 60 heartbeats per minute).

The exemplary embodiments allow separation of normal myocardium from abnormal myocardium due to irregular blood supply. The measurement of the peak flow (or FWHM) as representing a mean transit time and/or integrated value of the area under the curve provide differentiation of normal from abnormal myocardium. Since one can achieve temporal resolution of less than 100 ms, stress examination may not be required—and clearly Gd late enhancement examination is not required. The exemplary temporal resolution allows prediction of normal from abnormal myocardium. In addition, differentiation of treated and untreated infarct myocardium can be observed.

Figure 7:
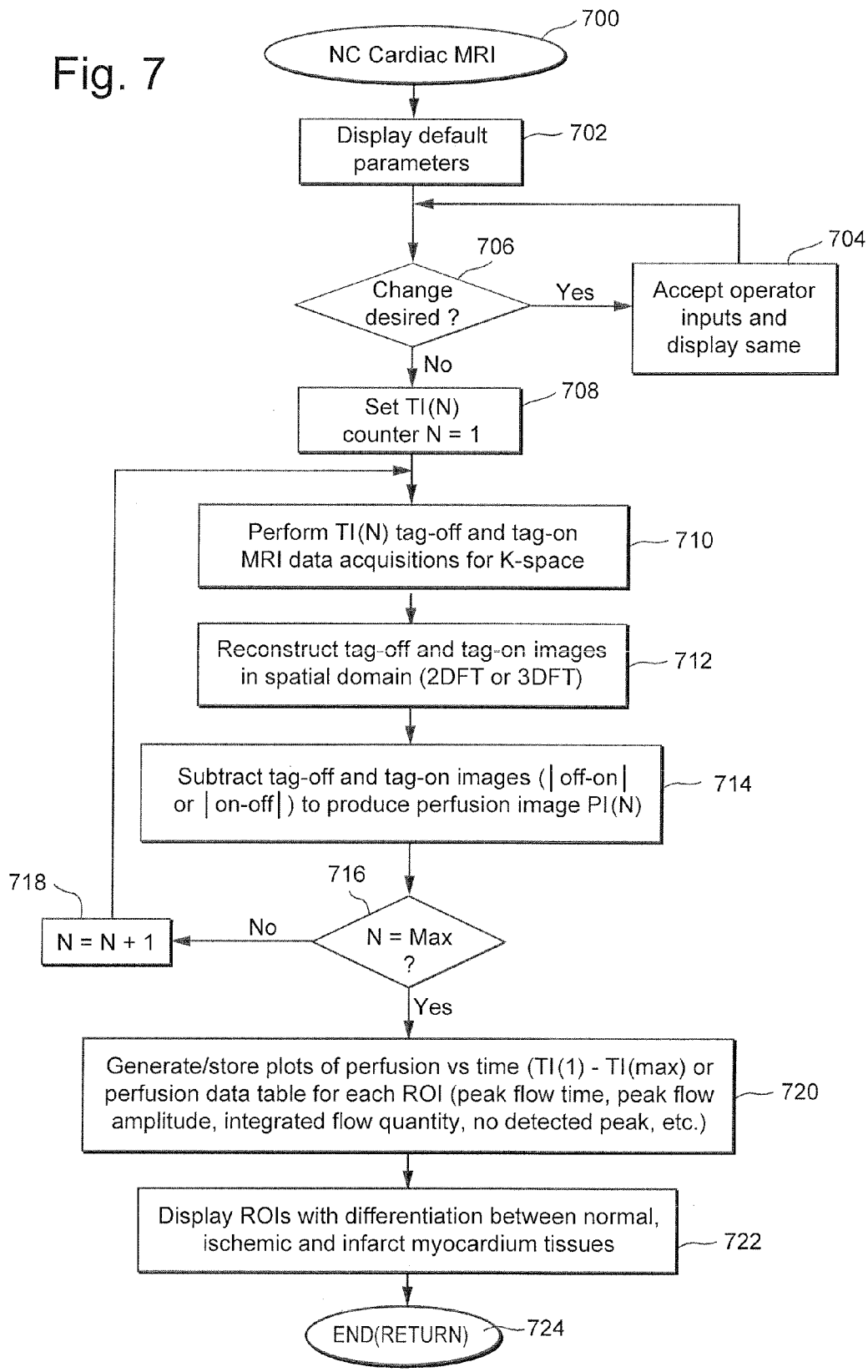
FIG. 7 is a schematic illustration of exemplary computer program code structure for use in the system of FIG. 1 in the form of a flow chart for implementing exemplary embodiments of non-contrast myocardial MRI capable of distinguishing between ischemic, infarct and normal myocardium based upon temporal and/or peak amplitude and/or integrated flow quantity.

In accordance with the stored program data code structures of FIG. 1, the non-contrast cardiac MRI subroutine 700 depicted at FIG. 7 can be entered via an appropriate overarching operating system or the like, as will be well understood by those in the art. Once entered, the subroutine 700 may display any number of desired default parameters at 702. For example, default parameters might specify possible data acquisition subsequences as being of the bSSFP type or the half-Fourier FSE or otherwise. Furthermore, the default parameters might include designation of whether or not a non-spatially selective 180° nutation pulse might be employed initially (in both tag-on and tag-off subsequences) so as to suppress background signals (as depicted in FIG. 2 as contrasted with FIG. 3) in the final perfusion image. One may also designate whether 2D or 3D data acquisition is desired. Of course, regions of interest can be designated manually or, perhaps, the standard AHA heart segments could be defaulted to as regions of interest. Whether one wants to use temporal discrimination, amplitude discrimination and/or integrated area under the curve discrimination for differentiating between normal, ischemic, infarct and revascularized infarct myocardium may be designated. The number of TI intervals and/or the value of such intervals may be among the default parameters that could be adjusted by the operator, if desired, at 704 (if such desire is selectively determined at 706).

Once all of the required NC cardiac MRI subroutine parameters have been determined (whether by default or by operator setting), then the TI counter N is initialized at 708. Tag-off/tag-on MRI data acquisitions for k-space for that particular TI(N) value are performed at 710, while suitable reconstruction of such k-space data into the spatial domain is achieved at 712. Then at 714, the generated tag-off/tag-on images are subtracted to produce a perfusion image data set for the current TI(N) value.

If the TI counter N has not yet reached its maximum value as tested at 716, then the counter is incremented at 718 and the processes of 710, 712 and 714 are repeated for another TI value.

Eventually, N will equal the maximum value and control will be passed to block 720 in FIG. 7. Here, acquired perfusion image data as a function of time is used to generate/store plots of perfusion v. time data and/or perfusion data table entries for each region of interest (e.g., peak flow times, peak flow amplitudes, integrated flow quantity, lack of detected peak, etc.). Thereafter, at 722, the ROIs may be displayed with differentiation between normal, ischemic and infarct myocardium values (e.g., see FIG. 5). If desired, perfusion curves for different ROIs can be superimposed. The subroutine 700 can be exited at 724 back to the higher level calling program code structure.

Although single shot FSE or FASE data acquisition sequences can be used as the actual data acquisition subsequence, the presently preferred data acquisition subsequences for the active phases of data acquisition are balanced steady-state free precession (bSSFP) sequences. For example, in FIG. 8 a Tag-On subsequence is depicted for perfusion flow-in using a selective tag pulse with 2D/3D bSSFP. The spatially selective RF tag pulse A is depicted in solid line while the optional non-selective inversion pulse B (for background suppression as previously noted) is depicted in dotted line. FIG. 9 depicts a similar Tag-Off subsequence (where the position of the tag pulse for the Tag-On sequence is also shown in dotted line for reference purposes). Notice that the same gradient magnetic pulses may be used at position A so as to maintain uniformity in this respect between the Tag-On and Tag-Off subsequences (even though there is no RF pulse A actually employed for the Tag-Off subsequence). FIG. 10 depicts the preferred Tag-on/Tag-off alternate acquisition process (i.e., in effect repeatedly concatenating a Tag-Off subsequence (e.g., FIG. 9) and a Tag-On subsequence (e.g., FIG. 8).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A magnetic resonance imaging (MRI) system comprising:
    an MRI gantry having static and gradient magnet assemblies and at least one radio frequency (RF) coil defining an image volume;
    MRI control circuits connected to control components within said MRI gantry and configured to effect MRI data acquisition sequences of RF and gradient magnetic pulses which elicit MRI signals, to acquire and process said elicited MRI signals into MR image data in conjunction (a) with use of an initial spatially selective nuclear magnetic resonance (NMR) RF tag pulse (tag-on) in a data acquisition subsequence and (b) without use of an initial spatially selective NMR RF tag pulse (tag-off) in a data acquisition subsequence;
    said MRI control circuits being configured to
    (a) acquire multi-dimensional MR k-space data from patient tissue using multiple said tag-on and tag-off data acquisition subsequences for each of multiple time to inversion (TI) intervals without using an injected contrast agent;
    (b) reconstruct said acquired k-space data into a series of spatial domain tag-on and tag-off MR image data, each having different TI intervals;
    (c) perform an analysis of TI dependence of signal intensity based on the series of spatial domain MR image data by (1) subtracting said tag-off and tag-on MR image data for each of plural TI intervals for each of plural regions of interest (ROI) to produce difference image data, each said ROI being a multi-pixel segment representing part of a segmented region of said patient tissue and (2) generating, for each of the plural ROIs, based on combining together the difference image data for plural pixels within that ROI, a separate profile of signal intensity versus time data representing blood perfusion versus time for that ROI, the difference image data for plural pixels within that ROI being obtained by adding together, averaging, or combining pixels within the multi-pixel segment, wherein for each of the plural ROIs, a peak flow time and/or a peak blood flow magnitude, or lack thereof, of the function differentiates between normal, ischemic and infarct tissues; and (d) store and display a result of the analysis by plotting a plurality of functions, each of the plotted plurality of functions being the generated function corresponding to a respective one of the plural ROIs.

2. An MRI system as in claim 1, wherein said MRI control circuits are configured to display image data as the result of the analysis for a region of interest (ROI) at each of the multiple TI intervals, the image data defining a plot of relative blood flow as a function of time.

3. An MRI system as in claim 2, wherein said MRI control circuits are configured to acquire said peak flow time and/or relative peak MR signal magnitude values for each of plural myocardium ROIs.

4. An MRI system as in claim 3, wherein said MRI control circuits are configured to concurrently superimpose and display said plots for a plurality of different ROIs.

5. An MRI system as in claim 3, wherein at least one of said ROIs represents a segment of myocardium assigned to one of plural predetermined segments of a Bull's Eye display of myocardium.

6. An MRI system as in claim 1, wherein said MRI control circuits are configured to perform said analysis of TI dependence of signal magnitude for an operator-specified region of interest (ROI).

7. An MRI system as in claim 1, wherein said MRI control circuits are configured to perform said analysis of TI dependence of signal magnitude for an ROI chosen by an operator.

8. An MRI system as in claim 1, wherein said MRI control circuits are configured to display a curve showing TI dependence of the signal intensity as a result of the analysis.

9. An MRI system as in claim 1, wherein said MRI control circuits are configured to change temporal resolution of the TI intervals.

10. An MRI system as in claim 1, wherein said MRI control circuits are configured to store and/or display image data having values which are different for revascularized, normal, ischemic and infarct tissue.

11. An MRI system as in claim 1, wherein said tag-on data acquisition subsequences are effected alternately with said tag-off data acquisition sequences.

12. An MRI system as in claim 1, wherein said MRI control circuits are configured to perform said analysis of TI dependence of signal magnitude and differentiate between states of an ROI based on peak flow times, and wherein said peak flow time for normal tissue has an earlier occurring peak flow time as compared to the peak flow time for ischemic tissue, and wherein said MRI control circuits are configured to distinguish between normal and ischemic tissue based on this temporal difference.

13. An MRI system as in claim 12, wherein said peak flow time for revascularized tissue has an earlier occurring peak flow time as compared to the peak flow time for normal tissue and/or ischemic tissue, and wherein said MRI control circuits are configured to identify revascularized tissue based on this temporal difference.

14. An MRI system as in claim 1, wherein said MRI control circuits are configured to perform said analysis of TI dependence of signal magnitude and differentiate between states of an ROI based on relative peak MR signal magnitude values, and wherein said relative peak MR signal magnitude value for normal tissue has a relatively higher peak flow value as compared to the peak MR flow value for ischemic tissue, and wherein said MRI control circuits are configured to distinguish between normal and ischemic tissue based on this difference in relative signal magnitude.

15. A magnetic resonance imaging (MRI) method comprising:

(a) acquiring multi-dimensional MR k-space data from patient tissue using multiple data acquisition subsequences including at least one data acquisition subsequence with use of a nuclear magnetic resonance (NMR) RF tag pulse (tag-on) and at least one data acquisition subsequence without use of a NMR RF tag pulse (tag-off) for each of multiple time to inversion (TI) intervals without using an injected contrast agent;

(b) reconstructing said acquired k-space data into a series of spatial domain MR image data;

(c) performing an analysis of TI dependence of signal intensity versus time based on the series of MR image data by (1) subtracting said acquired tag-off and tag-on MR image data for each of plural TI intervals for each of plural regions of interest (ROI) to produce difference image data, each said ROI being a multi-pixel segment representing part of a segmented region of said patient tissue and (2) generating, for each of the plural ROIs, based on combining together the difference image data for plural pixels within that ROI, the difference image data for plural pixels within that ROI being obtained by adding together, averaging, or combining pixels within the multi-pixel segment, a separate profile of signal intensity versus time data representing blood perfusion versus time for that ROI, wherein for each of the plural ROIs, a peak blood flow time and/or a peak blood flow magnitude, or lack thereof, of the function differentiates between normal, ischemic and infarct myocardia tissues; and (d) storing and displaying a result of the analysis image data having values which are different for normal, ischemic and infarct tissues, by plotting a plurality of functions, each of the plotted plurality of functions being the generated function corresponding to a respective one of the plural ROIs.

* * * * *